(12) United States Patent
Michihata

(10) Patent No.: US 10,405,733 B2
(45) Date of Patent: Sep. 10, 2019

(54) MEDICAL SIGNAL PROCESSING DEVICE AND MEDICAL OBSERVATION SYSTEM

(71) Applicant: Sony Olympus Medical Solutions Inc., Tokyo (JP)

(72) Inventor: Taihei Michihata, Kanagawa (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 273 days.

(21) Appl. No.: 15/083,488

(22) Filed: Mar. 29, 2016

(65) Prior Publication Data

US 2016/0316995 A1  Nov. 3, 2016

(30) Foreign Application Priority Data

Apr. 30, 2015  (JP) .................................. 2015-093675
Feb. 4, 2016   (JP) .................................. 2016-020284

(51) Int. Cl.

| A61B 1/00 | (2006.01) |
|---|---|
| G06F 19/00 | (2018.01) |
| A61B 1/045 | (2006.01) |
| A61B 1/04 | (2006.01) |
| A61B 1/06 | (2006.01) |
| A61B 1/07 | (2006.01) |
| H04N 5/225 | (2006.01) |
| H04N 5/232 | (2006.01) |

(Continued)

(52) U.S. Cl.
CPC ...... *A61B 1/00006* (2013.01); *A61B 1/00009* (2013.01); *A61B 1/00013* (2013.01); *A61B 1/00117* (2013.01); *A61B 1/042* (2013.01); *A61B 1/045* (2013.01); *A61B 1/0669* (2013.01); *A61B 1/07* (2013.01); *G06F 19/321* (2013.01); *H04N 5/2256* (2013.01); *H04N 5/23203* (2013.01); *H04N 5/77* (2013.01); *H04N 5/907* (2013.01); *H04N 2005/2255* (2013.01)

(58) Field of Classification Search
CPC ............ A61B 1/00006; A61B 1/00009; A61B 1/00013; A61B 1/00117; A61B 1/045; A61B 1/0661; G06F 19/32; H04N 5/2354; H04N 2005/2255
USPC .......................................................... 348/43
See application file for complete search history.

(56) References Cited

U.S. PATENT DOCUMENTS

| 2006/0052664 A1* | 3/2006 | Julian ................... A61B 1/0053 600/146 |
|---|---|---|
| 2008/0027284 A1* | 1/2008 | Suda ................... A61B 1/00055 600/134 |

(Continued)

FOREIGN PATENT DOCUMENTS

JP   2009-61032   3/2009

*Primary Examiner* — Tung T Vo
(74) *Attorney, Agent, or Firm* — Oblon, McClelland, Maier & Neustadt, L.L.P.

(57) ABSTRACT

A medical signal processing device is communicably connected to a medical control device through a plurality of signal transmission paths and processes an image signal corresponding to a result obtained by examining an inside of a subject. The medical signal processing device includes a transmission signal processing unit configured to generate a plurality of image signals for transmission by distributing the image signal based on transmission failure information that indicates a transmission failure on a signal in the signal transmission paths.

6 Claims, 10 Drawing Sheets

(51) Int. Cl.
*H04N 5/77* (2006.01)
*H04N 5/907* (2006.01)

(56) References Cited

U.S. PATENT DOCUMENTS

| | | | | |
|---|---|---|---|---|
| 2008/0262299 | A1* | 10/2008 | Niida | A61B 1/05 600/110 |
| 2009/0058997 | A1* | 3/2009 | Kato | H04N 7/183 348/65 |
| 2009/0179985 | A1* | 7/2009 | Amling | G06F 19/327 348/65 |
| 2012/0320176 | A1* | 12/2012 | Tanaka | A61B 1/00006 348/65 |
| 2013/0096380 | A1* | 4/2013 | Matsuzawa | A61B 1/00013 600/109 |
| 2013/0158352 | A1* | 6/2013 | Imaizumi | A61B 1/00009 600/111 |
| 2013/0169775 | A1* | 7/2013 | Ono | A61B 1/00009 348/68 |
| 2014/0340496 | A1* | 11/2014 | Okawa | A61B 1/00006 348/65 |
| 2015/0164331 | A1* | 6/2015 | Burgess | A61N 7/02 600/410 |
| 2016/0206185 | A1* | 7/2016 | Kinouchi | A61B 1/04 |
| 2017/0095137 | A1* | 4/2017 | Kinouchi | A61B 1/04 |

\* cited by examiner

MEDICAL SIGNAL PROCESSING DEVICE AND MEDICAL OBSERVATION SYSTEM

CROSS-REFERENCE TO RELATED APPLICATIONS

This application claims the benefit of Japanese Priority Patent Application JP 2015-93675 filed Apr. 30, 2015, and Japanese Priority Patent Application JP 2016-020284 filed Feb. 4, 2016, the entire contents of which are incorporated herein by reference.

BACKGROUND

The present disclosure relates to a medical signal processing device that inputs an image signal corresponding to a result obtained by examining the inside of a subject and processes the image signal, and a medical observation system including the medical signal processing device.

In the past, in the medical field, an endoscope device is used to observe internal organs of a subject, for example, a patient. For example, the endoscope device includes an endoscope (hereinafter, referred to as a camera head), a control device, and a transmission cable. The endoscope includes an image sensor. The control device controls the operation of the camera head and displays an image of the inside of a subject on a display device by processing the image signal picked up by the image sensor. The transmission cable electrically connects the camera head and the control device and transmits various signals.

In recent years, an image sensor having a large number of pixels enabling an image observation with a higher resolution has been developed, and the application thereof to an endoscope device is being studied. In accordance with this trend, adaptation of an optical transmission system that transmits signals using laser light is also being studied, to transmit a large number of signals between the image sensor and the control device at a high speed (see, for example, Japanese Patent Application Laid-open No. 2009-61032).

SUMMARY

In general, the transmission cable and the control device are separable and are connected with connectors thereof. Thus, in the endoscope device, an image signal converted into an optical signal in the camera head cannot be transmitted to the control device with an optical cable. In other words, an optical signal is transmitted from the camera head to the control device, through an optical cable in a transmission cable, an optical connection unit of a connector of the transmission cable, an optical connection unit of a connector of the control device, and an optical cable in the control device. When the connection surfaces of the optical connection units through which the light passes are soiled or fogged, or when there is angle deviation between the optical paths of the optical connection units, the optical signal is attenuated and a transmission failure on the optical signal occurs, resulting in the problem that an image suitable for observation cannot be displayed.

The transmission failure on the optical signal also occurs when the cable is deteriorated over time or with use. A conventional electrical cable deteriorating over time or for other reasons tends to break after noise due to the deterioration is gradually superimposed on signals and appears as image noise. Thus, the operator can easily recognize the abnormal state at a relatively early stage. However, in the optical cable, the optical fiber portion breaks suddenly, and leads to image loss. Hence, there is the problem that an image may be lost during the procedure.

There is a need for a medical signal processing device and a medical observation system that can detect a transmission failure in an optical transmission path, and that can continuously transmit image signals to a control device, even if a transmission failure occurs in the optical transmission path.

According to one aspect of the present disclosure, there is provided a medical signal processing device that is communicably connected to a medical control device through a plurality of signal transmission paths and processes an image signal corresponding to a result obtained by examining an inside of a subject. The medical signal processing device includes a transmission signal processing unit configured to generate a plurality of image signals for transmission by distributing the image signal based on transmission failure information that indicates a transmission failure on a signal in the signal transmission paths.

According to another aspect of the present disclosure, there is provided a medical observation system including: a medical signal processing device that is communicably connected to a medical control device through a plurality of signal transmission paths and processes an image signal corresponding to a result obtained by examining an inside of a subject, the medical signal processing device including: a transmission signal processing unit configured to generate a plurality of image signals for transmission by distributing the image signal based on transmission failure information that indicates a transmission failure on a signal in the signal transmission paths; a plurality of signal transmission paths configured to transmit the image signals for transmission from the medical signal processing device; and a medical control device configured to detect a transmission failure on a signal in the signal transmission paths, and includes a received-signal processing unit that reproduces the image signal based on the image signals for transmission transmitted through the signal transmission paths, wherein either one of the medical signal processing device and the medical control device includes a control unit configured to control distribution of the image signal by the transmission signal processing unit based on a detection result of the transmission failure by the received-signal processing unit.

DETAILED DESCRIPTION

Figure 1:
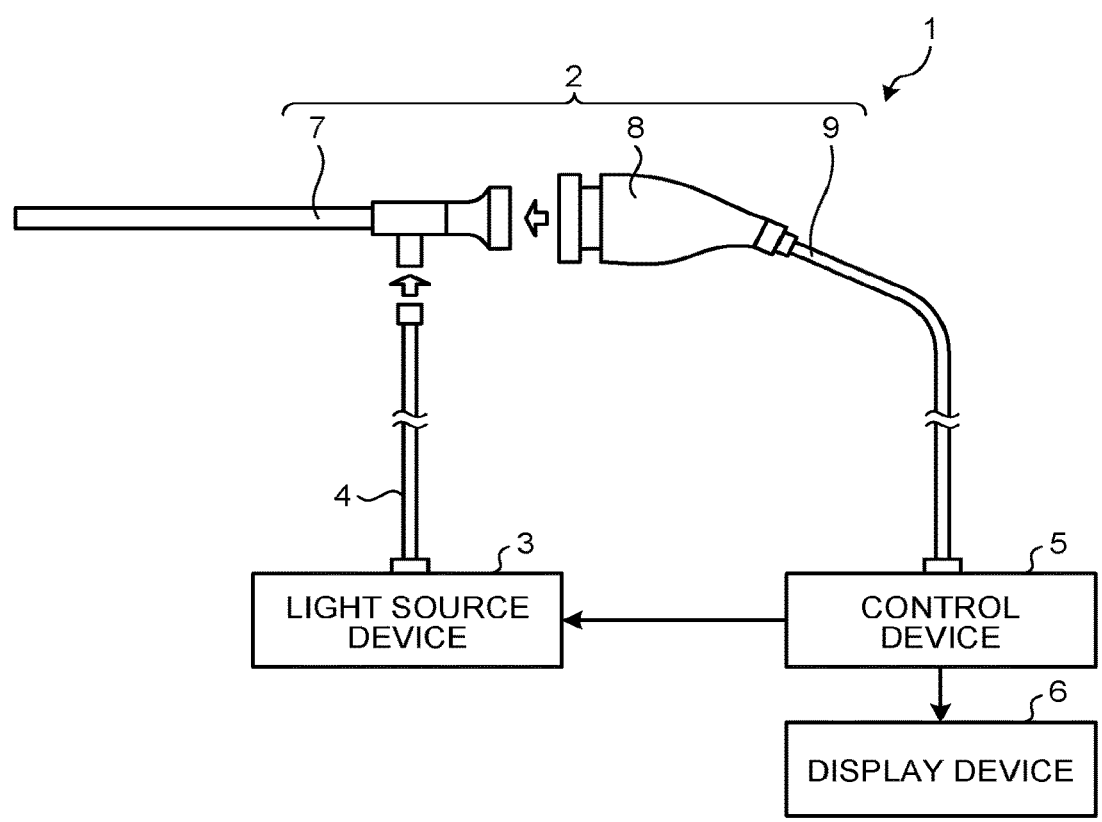
FIG. 1 is a schematic configuration diagram of a medical observation system according to a first embodiment of the present disclosure.

The following will describe endoscope devices as modes for carrying out the present disclosure (hereinafter, referred to as "embodiments"). However, the present disclosure is not limited to the embodiments. Further, in the drawings, the same reference numerals are given to the same components.

First Embodiment

FIG. 1 is a schematic configuration diagram of a medical observation system according to a first embodiment of the present disclosure. A medical observation system 1 is a system used in the medical field for observing the inside of an observation object, for example, a human body (inside the body). As illustrated in FIG. 1, the medical observation system 1 includes an endoscope 2, a light source device 3, a light guide 4, a control device 5, and a display device 6.

The endoscope 2 is used to examine inside the body (inside of a subject) and outputs the examination results. As illustrated in FIG. 1, the endoscope 2 includes an inserting unit 7, a camera head 8, and a transmission cable 9.

The inserting unit 7 is hard, has an elongated shape, and is to be inserted inside the body. The inserting unit 7 includes an optical system that includes one or more lenses and condenses an image of a subject.

The camera head 8 is detachably connected to the base end of the inserting unit 7. Under the control of the control device 5, the camera head 8 picks up an image of a subject condensed by the inserting unit 7, and outputs an image signal picked up. The camera head 8 photoelectrically converts the image signal into an optical signal and outputs it. The detailed configuration of the camera head 8 will be described below.

One end of the transmission cable 9 is detachably connected to the control device 5, and the other end is connected to the camera head 8. More specifically, the transmission cable 9 is obtained by arranging a plurality of electrical wires (not illustrated) and a plurality of optical cables (not illustrated) on the inside of the exterior covering, which is the outermost layer. The electrical wires each transmit a control signal, a synchronous signal, a clock, and electric power output from the control device 5 to the camera head 8. The optical cables transmit a plurality of image signals for transmission (optical signals) output from the camera head 8 to the control device 5. The transmission cable 9 of the first embodiment transmits the optical signals using an optical cable group 91. The transmission cable 9 also transmits electrical signals using a plurality of electrical wires 92. The optical cable group 91 includes four optical cables 91a to 91d each forming part of four signal transmission paths.

The light source device 3 is connected to one end of the light guide and supplies light to the one end of the light guide 4 to illuminate inside the body.

The one end of the light guide 4 is detachably connected to the light source device 3, and the other end thereof is detachably connected to the inserting unit 7. The light guide 4 transmits the light supplied from the light source device 3 from the one end to the other end, thereby supplying the light to the inserting unit 7. The light supplied to the inserting unit 7 is output from the tip end of the inserting unit 7 to illuminate the inside of the body. The light emitted to the inside of the body (image of a subject) is condensed by the optical system in the inserting unit 7.

The control device 5 includes a central processing unit (CPU) and other components, and integrally controls the operations of the camera head 8 and the display device 6. The control device 5 performs a predetermined image processing on an image signal picked up by the camera head 8. The detailed configuration of the control device 5 will be described below.

Under the control of the control device 5, the display device 6 displays various types of information including the image to which a predetermined image processing is performed by the control device 5. Thus, the operator can observe a desired position inside a subject and determine the properties thereof by operating the endoscope 2 while looking at the image (in-vivo image) displayed on the display device 6. The display device 6 includes a liquid crystal display, an organic electroluminescence (EL) display, or the like.

Figure 2:
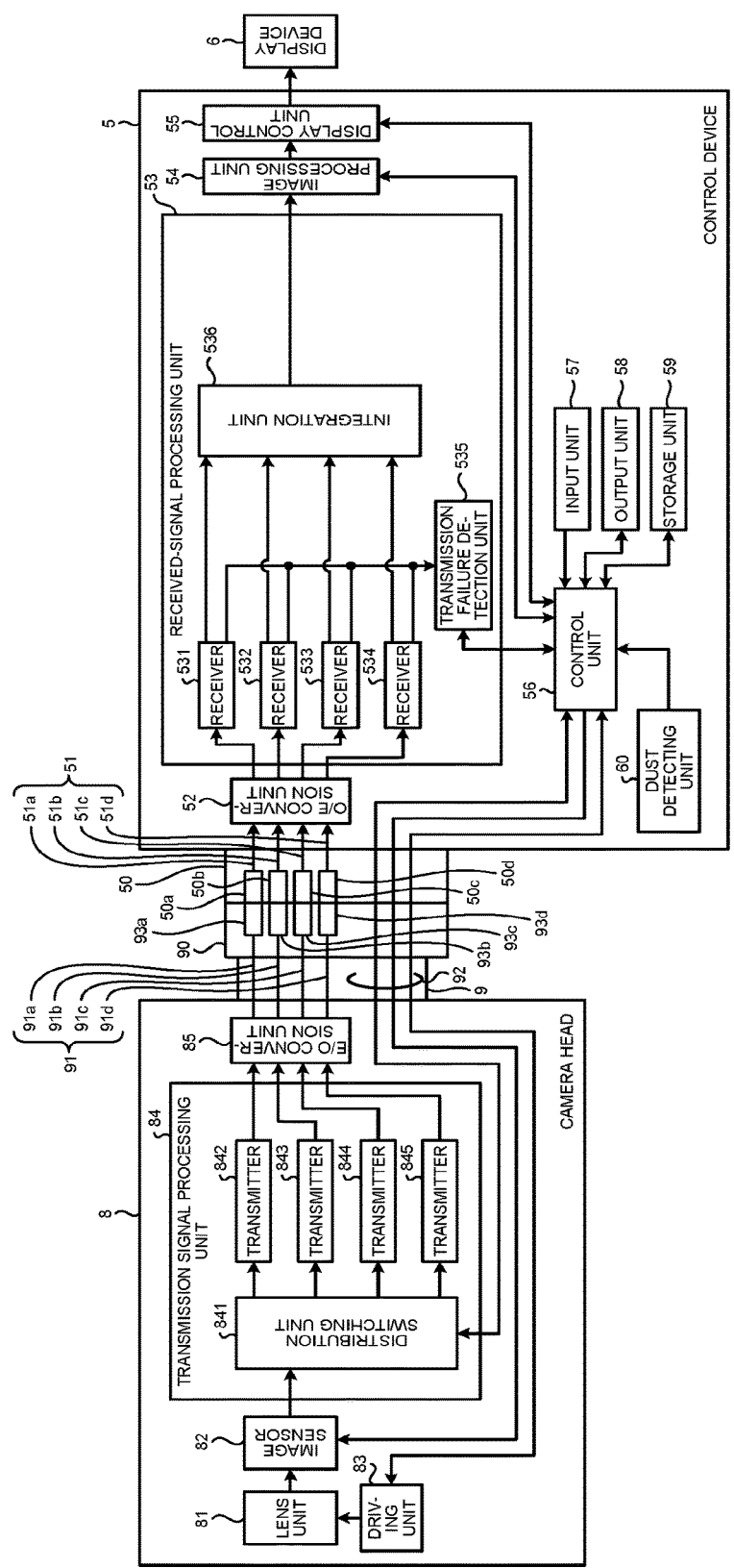
FIG. 2 is a block diagram of a configuration of a camera head, a transmission cable, and a control device of an endoscope illustrated in FIG. 1.

Next, a configuration of the camera head 8, the transmission cable 9, and the control device 5 will now be described. FIG. 2 is a block diagram of a configuration of the camera head 8, the transmission cable 9, and the control device 5 of the endoscope 2.

As illustrated in FIG. 2, the camera head 8 includes a lens unit 81, an image sensor 82, a driving unit 83, a transmission signal processing unit 84, and an E/O conversion unit 85 (electrical-to-optical conversion unit).

The lens unit 81 includes one or more lenses and forms an image of a subject condensed by the inserting unit 7 on an imaging surface of the image sensor 82. The lens or lenses are movable along an optical axis. The lens unit 81 further includes an optical zoom mechanism (not illustrated) for changing the angle of view by moving the lens or lenses and a focus mechanism (not illustrated) for changing the focal point by moving the lens or lenses.

Under the control of the control device 5, the image sensor 82 picks up an image of the inside of a subject. The image sensor 82 includes a light receiving unit (not illustrated), a reading unit (not illustrated), an analog front end (AFE) unit (not illustrated), and a control unit (not illustrated). The light receiving unit includes a plurality of pixels disposed in a matrix array each receiving light from the subject irradiated with light and generating an image signal by photoelectrically converting the received light. The reading unit reads out the image signals (electrical signals) generated by the pixels. The AFE unit performs noise reduction and analog-to-digital (A/D) conversion on the image signal (analog) read out by the reading unit. The control unit controls the operation of the image sensor 82 in accordance with the control signal received from the control device 5. The image sensor 82 outputs a digital image signal. For example, the image sensor 82 is a complementary metal oxide semiconductor (CMOS) image sensor that can expose and read out each horizontal line. The image sensor 82 may be a charge coupled device (CCD) image sensor. The image signal generated by the image sensor 82 is output to the transmission signal processing unit 84, as a live image signal in a RAW format or as an image signal in a predetermined format with a low compression rate.

Under the control of the control device 5, the driving unit 83, operates the optical zoom mechanism and focus mechanism and changes the angle of view and focal point of the lens unit 81.

The transmission signal processing unit 84 includes a distribution switching unit 841 and four transmitters 842 to 845.

The distribution switching unit 841 receives transmission failure information that indicates a signal failure in the four signal transmission paths from the control device 5. The distribution switching unit 841 generates and outputs, to the four transmitters 842 to 845, a plurality of distribution image signals by switching the distribution method of the image signals based on the transmission failure information. For example, when all four optical cables are functioning normally, the distribution switching unit 841 distributes the image signals to the four transmitters. When a transmission failure is detected in m pieces (m=1, 2, or 3) of signal transmission paths, the distribution switching unit 841 distributes the image signals to 4−m pieces of transmitters, excluding the transmitter corresponding to the signal transmission path in failure. The distribution switching unit 841 changes the transmission rate corresponding to the number of the image signals to be distributed. In this case, the distribution switching unit 841 changes the transmission rate of the distribution image signals, so that the total transmission rate becomes equal, regardless of the number of distribution. In the first embodiment, each of the image signals distributed by the distribution switching unit 841 is a parallel signal.

The transmitters 842 to 845 perform encoding processing, parallel/serial (P/S) conversion processing, and other operations on the distribution image signals received from the distribution switching unit 841, and output the resultant signals to the E/O conversion unit 85. For example, the transmitters 842 to 845 perform encoding processing of N-bit/M-bit encoding (N<M). For example, the transmitters 842 to 845 perform 8$b$/10$b$ encoding processing, 64$b$/66$b$ encoding processing, or 128$b$/130$b$ encoding processing on the received distribution image signals, based on the stored conversion table. The transmitters 842 to 845 perform processing such as superimposition processing of a clock signal, K-code insertion processing to the starting position and the finishing position of valid data, and the P/S conversion on the distribution image signals to which encoding processing is applied. The transmitters 842 to 845 then serially output the resultant signals to the E/O conversion unit 85.

For example, the transmission signal processing unit 84 described above includes a dedicated integrated circuit, such as a field programmable gate array (FPGA).

The E/O conversion unit 85 converts the serial distribution image signals input from the transmitters 842 to 845 into optical signals, and outputs the resultant optical signals to the corresponding optical cables 91$a$ to 91$d$. For example, when four image signals are input, the E/O conversion unit 85 outputs four optical signals to the corresponding four optical cables. When three electrical signals are input, the E/O conversion unit 85 outputs three optical signals to the corresponding three optical cables. For example, the E/O conversion unit 85 includes a laser diode and a light output unit that outputs light for communication such as laser light.

The optical transmission performance of the light output unit described above may deteriorate resulting from the decrease in the quantity of output light due to long driving hours. Thus, the medical observation system 1 may include a replacement time notification unit that sends notification of a replacement time of the light output unit. The replacement time notification unit includes an energizing time counting unit, a non-volatile memory, a comparing unit, and a notification unit. The energizing time counting unit counts the energizing time in which the light output unit is energized. The non-volatile memory stores therein energizing time information obtained by the energizing time counting unit. The comparing unit compares the energizing time information stored in the non-volatile memory and a certain replacement time determined in advance. When the comparing unit indicates that the energizing time has exceeded the replacement time, the notification unit sends notification of the fact.

The notification from the notification unit may be sent when the energizing time has exceeded the replacement time, at a predetermined time before the replacement time, or at both times. The predetermined time described above may be appropriately set based on the notification time.

The medical observation system 1 may include a light quantity measurement unit that measures at least part of the quantity of light from the light output unit, instead of the energizing time counting unit. In this case, the notification unit may send notification when the light quantity becomes equal to or less than a predetermined value.

For example, the operator or a service technician who receives the notification from the notification unit replaces the transmission cable 9. However, components to be replaced are not limited the transmission cable 9, but may be the light output unit or the E/O conversion unit 85. For example, when the light output unit is provided on the camera head 8 instead of the transmission cable 9, the operator or the service technician replaces the camera head 8. In this manner, it is possible to implement optical transmission that does not deteriorate the performance.

The transmission cable 9 includes a connector 90 (transmission side connector) detachably connected to a connector 50 of the control device 5, which will be described below, an optical cable group 91 composed of the four optical cables 91$a$ to 91$d$, and the electrical wires 92.

The tip ends of the optical cables 91$a$ to 91$d$ are connected to the E/O conversion unit 85, and the base ends of the optical cables 91$a$ to 91$d$ include optical connection units 93$a$ to 93$d$ (transmission side optical connection units), respectively. The optical connection units 93$a$ to 93$d$ are provided in the connector 90. Each of the optical connection units 93$a$ to 93$d$ includes a gradient index (GRIN) lens to be connected to an optical fiber end surface of each of the corresponding optical cables 91$a$ to 91$d$, and a cover glass that covers the surface of the GRIN lens.

The control device 5 includes the connector 50 (reception side connector), an optical cable group 51 including a plurality of optical cables 51$a$ to 51$d$, an O/E conversion unit 52 (optical-to-electrical conversion unit), and a received-signal processing unit 53, an image processing unit 54, a display control unit 55, a control unit 56, an input unit 57, an output unit 58, a storage unit 59, and a dust detecting unit 60.

The connector 50 includes optical connection units 50$a$ to 50$d$ (reception side optical connection units). The optical cables 51$a$ to 51$d$ extend from the corresponding optical connection units 50$a$ to 50$d$. The optical connection units 50$a$ to 50$d$ are provided at the tip ends serving as the input side ends of the corresponding optical cables 51$a$ to 51$d$, and separably connected to the optical connection units 93a to 93d in the connector 90 of the transmission cable 9, which is an exterior member. Each of the optical connection units 50a to 50d includes a GRIN lens to be connected to an optical fiber end surface of each of the optical cables 51a to 51d, and a cover glass that covers the surface of the GRIN lens. An optical connection unit 50X (X=a, b, c, or d. Hereinafter, the same character is used in a corresponding manner) and an optical connection unit 93X at the side of the transmission cable 9 connect an optical cable 91X and an optical cable 51X, by bringing the connection surfaces thereof in contact with each other. The optical cables 51X and 91X and the optical connection units 50X and 93X form one signal transmission path. In the first embodiment, the number of the signal transmission paths is not limited to four, but may be two, three, or five or more.

The optical cables 51a to 51d transmit optical signals input to the corresponding optical connection units 50a to 50d, and input the transmitted optical signals to the O/E conversion unit 52.

The O/E conversion unit 52 converts the optical signals transmitted through the optical cables 51a to 51d into a plurality of serial electrical signals and inputs the electrical signals to the received-signal processing unit 53.

The received-signal processing unit 53 includes four receivers 531 to 534, a transmission failure detection unit 535, and an integration unit 536. The receivers 531 to 534 receive the serial electrical signals converted by the O/E conversion unit 52. The transmission failure detection unit 535 detects a transmission failure based on the reception state of the receivers 531 to 534. The integration unit 536 integrates and outputs the signals output from the receivers 531 to 534.

The receivers 531 to 534 execute clock data recovery (CDR) processing, serial-to-parallel (S/P) conversion processing, K-code detection processing, bit error rate (BER) detection processing, and encoding processing. The CDR processing reproduces a clock signal superimposed on the serial signal received from the O/E conversion unit 52. The S/P conversion processing converts the serial signal, on which the CDR processing is performed, into a parallel signal. The K-code detection processing acquires valid data by detecting a K-code from the parallel signal, to which the S/P conversion is performed. The BER detection processing calculates the probability of receiving incorrect data from the parallel signal, to which the S/P conversion is performed. The encoding processing performs M bit/N bit conversion (encoding) on the parallel signal, to which the K-code detection processing is performed. The receivers 531 to 534 output the execution results of the CDR processing, the K-code detection processing, and the BER detection processing to the transmission failure detection unit 535.

The transmission failure detection unit 535 detects the presence of a transmission failure on an optical signal in the signal transmission paths based on the execution results of the CDR processing, the K-code detection processing, and the BER detection processing executed by the receivers 531 to 534, and specifies the signal transmission path in which the transmission failure has occurred. The transmission failure detection unit 535 outputs transmission failure information to the control unit 56. The transmission failure information includes at least information that indicates the signal transmission path in which the transmission failure has occurred.

The integration unit 536 executes processing reverse to the processing executed by the distribution switching unit 841 of the camera head 8 using the parallel electrical signals output from the receivers 531 to 534, thereby integrating the electrical signals. The integration unit 536 performs integration processing appropriate to the number of parallel electrical signals received from the receivers 531 to 534. When a transmission failure occurs in any of the four signal transmission paths, loss occurs in the signals integrated by the integration unit 536, losing the amount of image data corresponding to the transmission failure having occurred.

For example, the received-signal processing unit 53 described above includes a dedicated integrated circuit, such as an FPGA, as with the transmission signal processing unit 84.

Under the control of the control unit 56, which will be described below, the image processing unit 54 performs predetermined signal processing on the image signal output from the received-signal processing unit 53, in other words, on the image signal generated by the image sensor 82 in the RAW format or in a predetermined format with a low compression rate. The image processing unit 54 executes, on this image signal, various types of image processing including optical black subtraction processing, gain adjustment processing, image signal synchronization processing, gamma correction processing, white balance (WB) adjustment processing, color matrix arithmetic processing, color reproduction processing, edge emphasizing processing, and other operations.

The display control unit 55 generates an image signal for display causing the display device 6 to perform display from the image signal processed by the image processing unit 54. For example, the image signal for display output to the display device 6 is a digital signal in a format, such as the serial digital interface (SDI), the Digital Visual Interface (DVI) (registered trademark), or the High-Definition Multimedia Interface (HDMI) (registered trademark). When the transmission failure detection unit 535 detects a transmission failure in a signal transmission path, under the control of the control unit 56, the display control unit 55 generates an alarm image signal indicating that a transmission failure has occurred in the signal transmission path, and outputs and displays the generated alarm image signal on the display device 6. When an accumulation amount of dust detected by the dust detecting unit 60 exceeds a predetermined threshold, under the control of the control unit 56, the display control unit 55 generates an alarm image signal indicating that abnormal temperature rise may occur in the equipment, and outputs and displays the generated alarm image signal on the display device 6.

For example, the control unit 56 is implemented using a CPU and other components. The control unit 56 controls processing operations of the units in the control device 5. The control unit 56 controls the operation of the control device 5 by, for example, transmitting instruction information and data to the units in the control device 5. The control device 5 is connected to the components of the camera head 8 through the cables, and controls the operations of the image sensor 82, the driving unit 83, and other components. The control unit 56 also controls the distribution switching processing performed by the distribution switching unit 841 of the camera head 8.

The control unit 56 changes the number of electrical signals to be output from the transmission signal processing unit 84 appropriate to the detection results output by the transmission failure detection unit 535. When the transmission failure detection unit 535 specifies a signal transmission path in which a transmission failure has occurred among the signal transmission paths, the control unit 56 generates a distribution switching control signal that changes the number of distribution image signals to be output from the transmission signal processing unit 84 so that the optical signals are distributed to the signal transmission paths excluding the signal transmission path in which the transmission failure has occurred. The control unit 56 then transmits the distribution switching control signal to the transmission signal processing unit 84 of the camera head 8.

The input unit 57 is implemented with operating devices, such as a mouse, a keyboard, and a touch panel, and receives an input of various types of instruction information of the medical observation system 1. More specifically, the input unit 57 receives inputs of various types of instruction information such as information on the subject (such as an ID, date of birth, and name), identification information of the endoscope 2 (such as an ID and items corresponding to the examination), and examination contents.

For example, the output unit 58 is implemented with a speaker, a printer, and other devices, and outputs various types of information related to the in-vivo observation. When the transmission failure detection unit 535 detects a transmission failure, under the control of the control unit 56, the output unit 58 outputs an alarm sound that indicates that the transmission failure has occurred. When an accumulation amount of dust detected by the dust detecting unit 60 exceeds a predetermined threshold, under the control of the control unit 56, the output unit 58 outputs an alarm sound that indicates that abnormal temperature rise may occur in the equipment.

The storage unit 59 is implemented with a volatile memory, such as a random access memory (RAM), and a non-volatile memory, such as a read only memory (ROM), and stores therein various programs to operate the camera head 8, the control device 5, and other devices. The storage unit 59 temporarily stores therein information that is being processed by the control device 5. The storage unit 59 stores therein an image signal picked up by the image sensor 82, and an image signal on which image processing is performed by the image processing unit 54. The storage unit 59 may be implemented with a memory card and other medium attached from the outside of the control device 5.

The dust detecting unit 60 detects the accumulation of dust in the control device 5, and outputs the detection result to the control unit 56. When an accumulation amount of dust detected by the dust detecting unit 60 exceeds a predetermined threshold, the control unit 56 outputs, to the display device 6 or the output unit 58, alarm information indicating that the fan may have locked up or abnormal temperature rise due to a short circuit or reduction of air flow resulting from the accumulation of dust may occur in the equipment.

Figure 3:
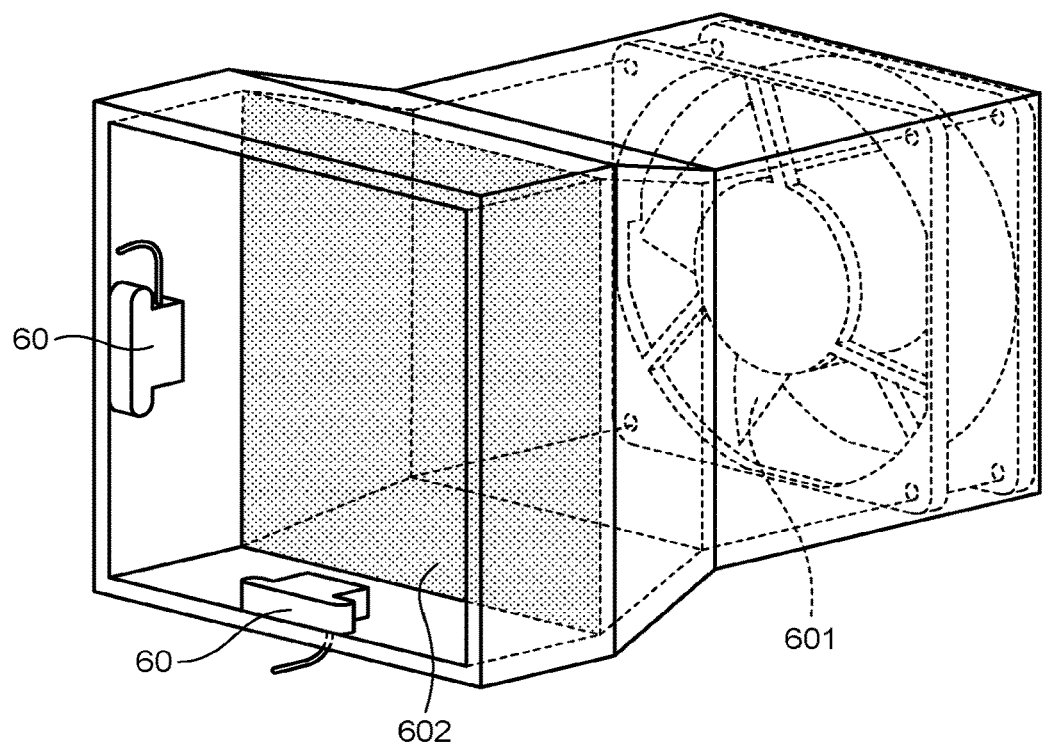
FIG. 3 is a perspective view of part of the inside of the control device illustrated in FIG. 2.
Figure 4:
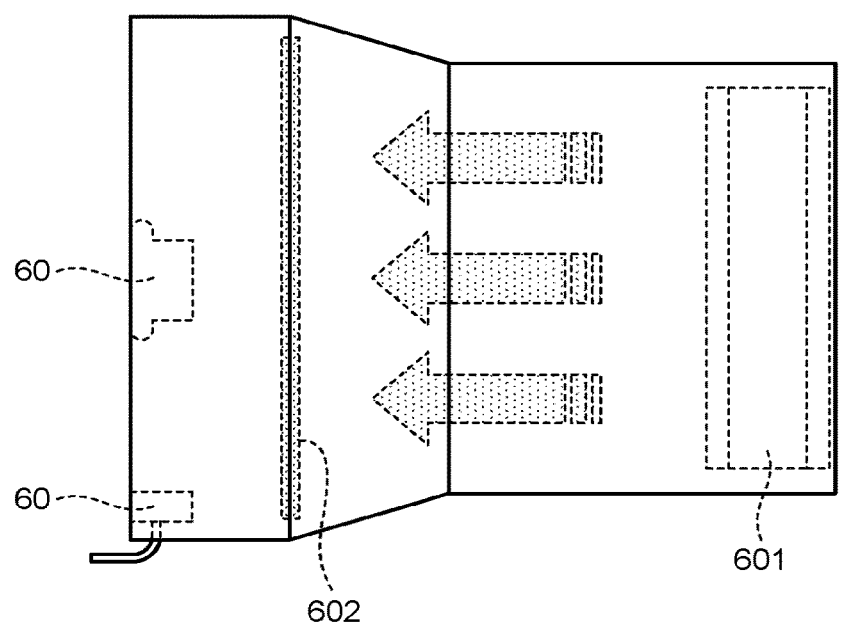
FIG. 4 is a right side elevation view of part of the inside of the control device illustrated in FIG. 3.

FIG. 3 is a perspective view illustrating part of the inside of the control device 5. For example, a plurality (two in FIG. 3) of flow sensors, each serving as the dust detecting unit 60, are provided outside a filter 602 at the side of an air outlet of a fan 601 of the control device 5. FIG. 4 is a right side elevation view of part of the inside of the control device 5 illustrated in FIG. 3. The dust detecting unit 60 detects the amount of air that flows to the outside from the fan 601, as illustrated in an arrow in FIG. 4. The amount of air is reduced as dust is accumulated on the filter 602. Thus, when the value of the amount of air detected by the dust detecting unit 60 falls below a predetermined threshold, the control unit 56 performs output control processing of the alarm information.

The dust detecting unit 60 may be an optical sensor that optically detects dust. In this case, the dust detecting unit 60 is installed at a position where dust is easily accumulated, and when the detected amount of dust exceeds the threshold, the control unit 56 performs output control processing of the alarm information. The dust detecting unit 60 may be a circuit dedicated to detect dust. When a short circuit due to dust has occurred on the circuit, the control unit 56 performs output control processing of the alarm information. The dust detecting unit 60 may be installed at the vicinity of at least one of the fan 601 and the filter 602, or may be installed at a corner of a case where dust is easily accumulated. FIG. 3 and FIG. 4 illustrate an example of installing two dust detecting units 60. However, a single dust detecting unit 60 may be installed, or three or more dust detecting units 60 may be installed.

Figure 5:
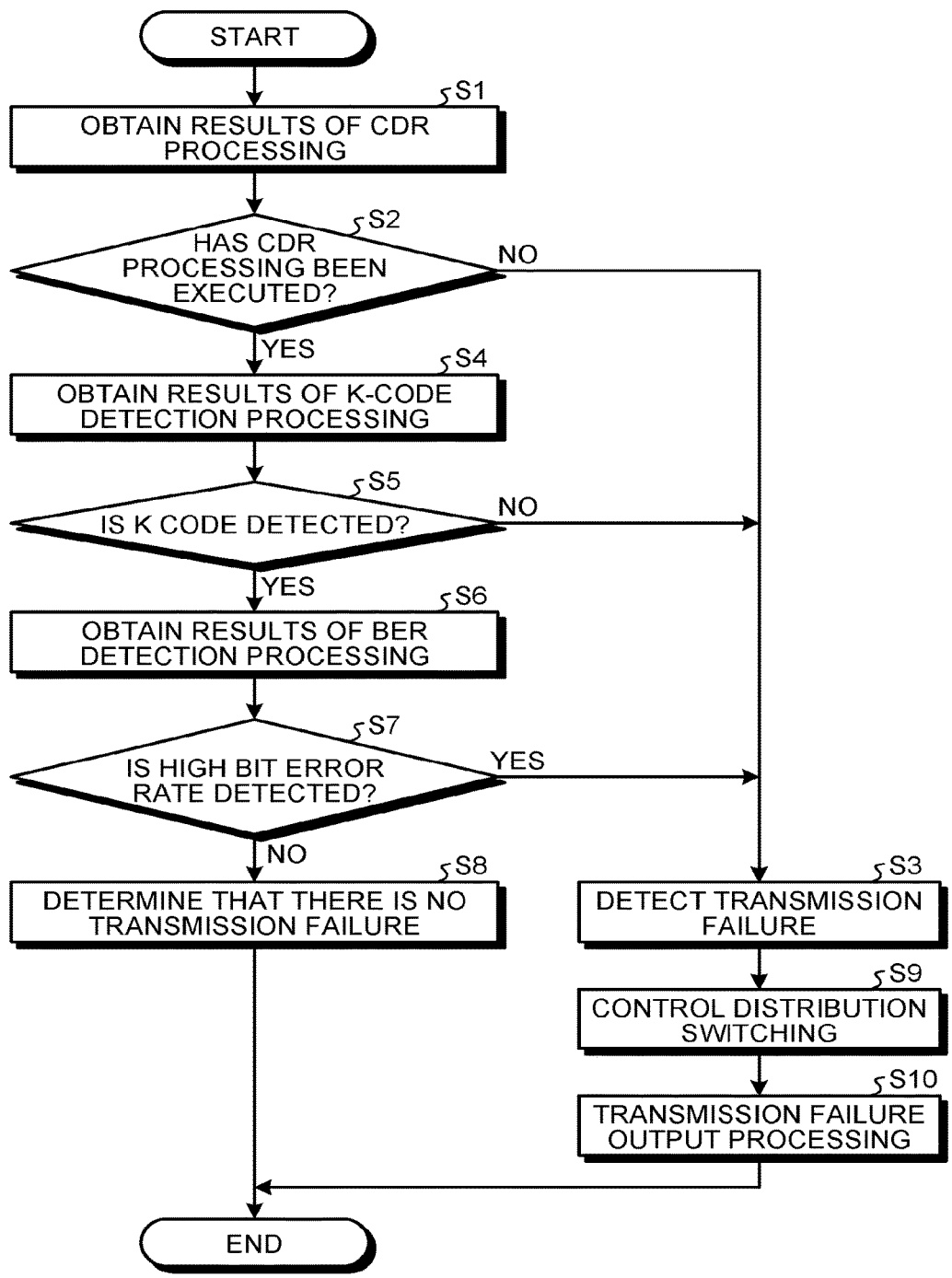
FIG. 5 is a flowchart of a processing procedure for transmission failure detection in the control device illustrated in FIG. 2.

Processing for transmission failure detection in the control device 5 illustrated in FIG. 2 will now be described. FIG. 5 is a flowchart of a processing procedure for transmission failure detection in the control device 5 illustrated in FIG. 2.

As illustrated in FIG. 5, the transmission failure detection unit 535 obtains results of the CDR processing from the receivers 531 to 534 (step S1), and determines whether the receivers have executed the CDR processing (step S2). When an optical fiber is disconnected, an optical signal is not input to the control device 5 of the reception side, from the optical cable that includes the disconnected optical fiber. Thus, the CDR processing will not be performed. Hence, when a receiver cannot execute the CDR processing (No at step S2), the transmission failure detection unit 535 detects that a transmission failure caused by the disconnection or other reasons has occurred in the signal transmission path corresponding to the receiver (step S3).

If it is determined that all the receivers have executed the CDR processing (Yes at step S2), the transmission failure detection unit 535 obtains the results of the K-code detection processing from the receivers 531 to 534 (step S4). Based on the obtained results of the K-code detection processing, the transmission failure detection unit 535 determines whether the receivers have detected a K-code (step S5). When an optical fiber is disconnected, an optical signal is not input to the control device 5 of the reception side, from the optical cable that includes the disconnected optical fiber. Thus, detection of the K-code or detection of data timing will not be performed. Hence, when a receiver cannot detect the K-code (No at step S5), the transmission failure detection unit 535 detects that a transmission failure has occurred in the signal transmission path corresponding to the receiver (step S3).

If it is determined that all the receivers have detected the K-code (Yes at step S5), the transmission failure detection unit 535 obtains the results of the BER detection processing from the receivers 531 to 534 (step S6). Based on the obtained results of the BER detection processing, the transmission failure detection unit 535 determines whether the bit error rate of each receiver is a high bit error rate exceeding a predetermined threshold (step S7). If transmission failure or transmission deterioration occurs in the optical cable, the intensity of the optical signal input to the O/E conversion unit 52 weakens, thereby increasing the bit error rate detected by the BER detection processing. Thus, when the bit error rates in the results of the BER detection processing from all the receivers are not high bit error rates (No at step S7), the transmission failure detection unit 535 determines that there is no transmission failure (step S8), and finishes this processing for transmission failure detection.

If a receiver has a high bit error rate as the result of the BER detection processing (Yes at step S7), the transmission failure detection unit 535 detects that a transmission failure has occurred in the signal transmission path corresponding to the receiver (step S3).

Processes subsequent to step S3 will now be described. The control unit 56 transmits, to the transmission signal processing unit 84, a distribution switching control signal for distributing image signals to the transmitters corresponding to the optical cables excluding the optical cable specified by the transmission failure detection unit 535 (step S9).

The control unit 56 performs transmission failure output processing that causes the display device 6 and the output unit 58 to output the alarm information indicating that the transmission failure has occurred (step S10). This alarm information specifies and indicates the signal transmission path in which the transmission failure has occurred. The alarm information also indicates a method for recovering from the transmission failure. For example, in a signal transmission path on which the CDR processing or the K-code detection processing is not executed, there is a high possibility that an optical fiber is disconnected. Thus, a message that recommends, for example, maintenance to replace the optical cable is output after the examination is completed. In a signal transmission path on which a high bit error rate is detected as a result of the BER detection processing, there is a possibility that the optical connection unit of the connector is soiled or fogged. Hence, a message that recommends cleaning the optical connection unit is output after the examination is completed. In this case, there is a possibility that the optical axes of the optical connection units may be deviated. Thus, a message that recommends optical axis correction is also output.

For example, in the control device 5, the processes from step S1 to step S10 may be performed during the examination, or the processes from step S1 to step S10 may be performed during the pre-operational inspection or after the examination is completed.

In this manner, in the first embodiment, even if a transmission failure occurs in one of the optical cables during the procedure, it is possible to switch to other three signal transmission paths in which a transmission failure has not occurred. Thus, the optical signals (image signals) are continuously transmitted to the control device 5. Consequently, in the first embodiment, for example, even if a transmission failure occurs in the signal transmission path during the procedure, it is possible to prevent sudden image loss during the procedure without fail. Thus, it is possible to appropriately continue the procedure. In the first embodiment, even if a communication failure occurs resulting from the soiled optical connection unit, the optical axis deviation, or the deterioration over time, it is possible to prevent image noise due to the transmission failure. Thus, it is possible to continuously display a clear image without noise. Also, in the first embodiment, alarm information is output when a transmission failure is detected in the optical connection unit. Thus, the transmission failure will be taken care of.

Figure 6:
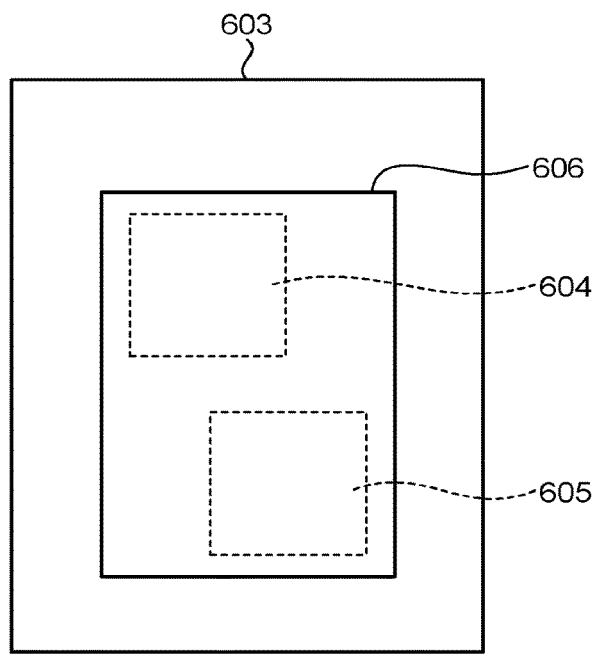
FIG. 6 is an example of a plan view of an essential part inside a case of the control device illustrated in FIG. 2.
Figure 7:
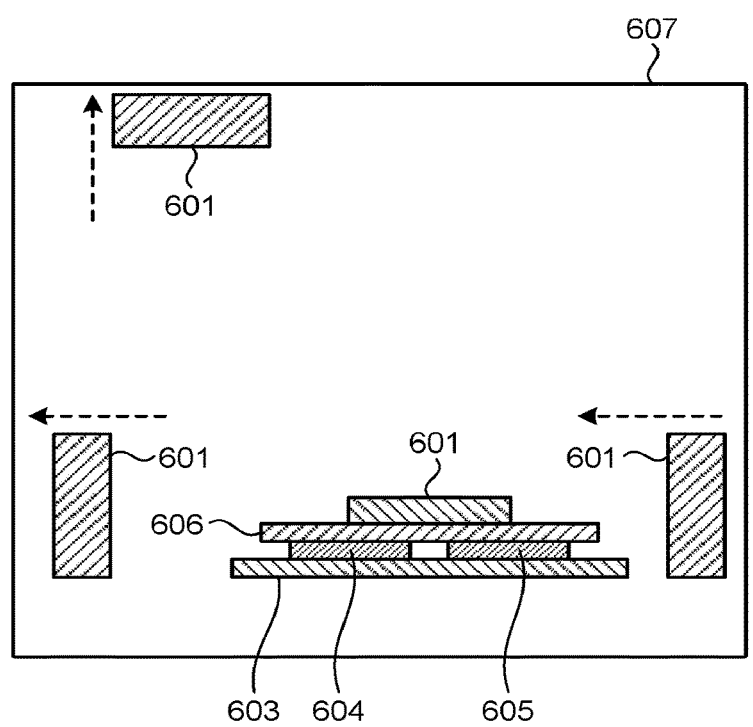
FIG. 7 is a view obtained by cutting the case illustrated in FIG. 6 by a plane vertical to the surface of a substrate in the case.

FIG. 6 is an example of a plan view of an essential part inside a case of the control device 5. FIG. 7 is a view obtained by cutting the case illustrated in FIG. 6 by a plane vertical to the surface of a substrate in the case. As illustrated in FIG. 6 and FIG. 7, devices that execute various types of processing, such as image pickup, are connected to a substrate 603 provided inside the case of the control device 5. In general, the devices generate heat while being driven. Thus, a fan or the like is usually provided to cool the devices that generate heat. However, if the fan has locked up, the devices on the substrate may be damaged due to the generated heat. Hence, in the first embodiment, instead of providing a dedicated fan for each chip, a plurality of devices 604 and 605 are connected by a heat sink 606 that is a high thermal conductive member. By cooling the heat sink 606 using a plurality of fans 601 in a case 607 including the fan 601 provided on the heat sink 606, it is possible to prevent the risk of a single failure of a cooling unit, such as the locking of the fan. When the single failure such as the locking of the fan occurs, the control unit 56 performs output control processing of the alarm information.

The cooling unit described above may be applied to the camera head 8. When the cooling unit is applied to the camera head 8, the camera head 8 is preferably cooled by heat radiation caused by heat transmission to the case and other components, instead of using a cooling fan. When abnormal heat is generated in the camera head 8, the camera head 8 notifies the control device 5 of the fact.

If the transmission failure detection unit 535 detects a transmission failure in one of the four signal transmission paths, it is possible to transmit optical signals through a certain pair of signal transmission paths, instead of using the remaining three signal transmission paths.

Modification 1-1 of First Embodiment

Figure 8:
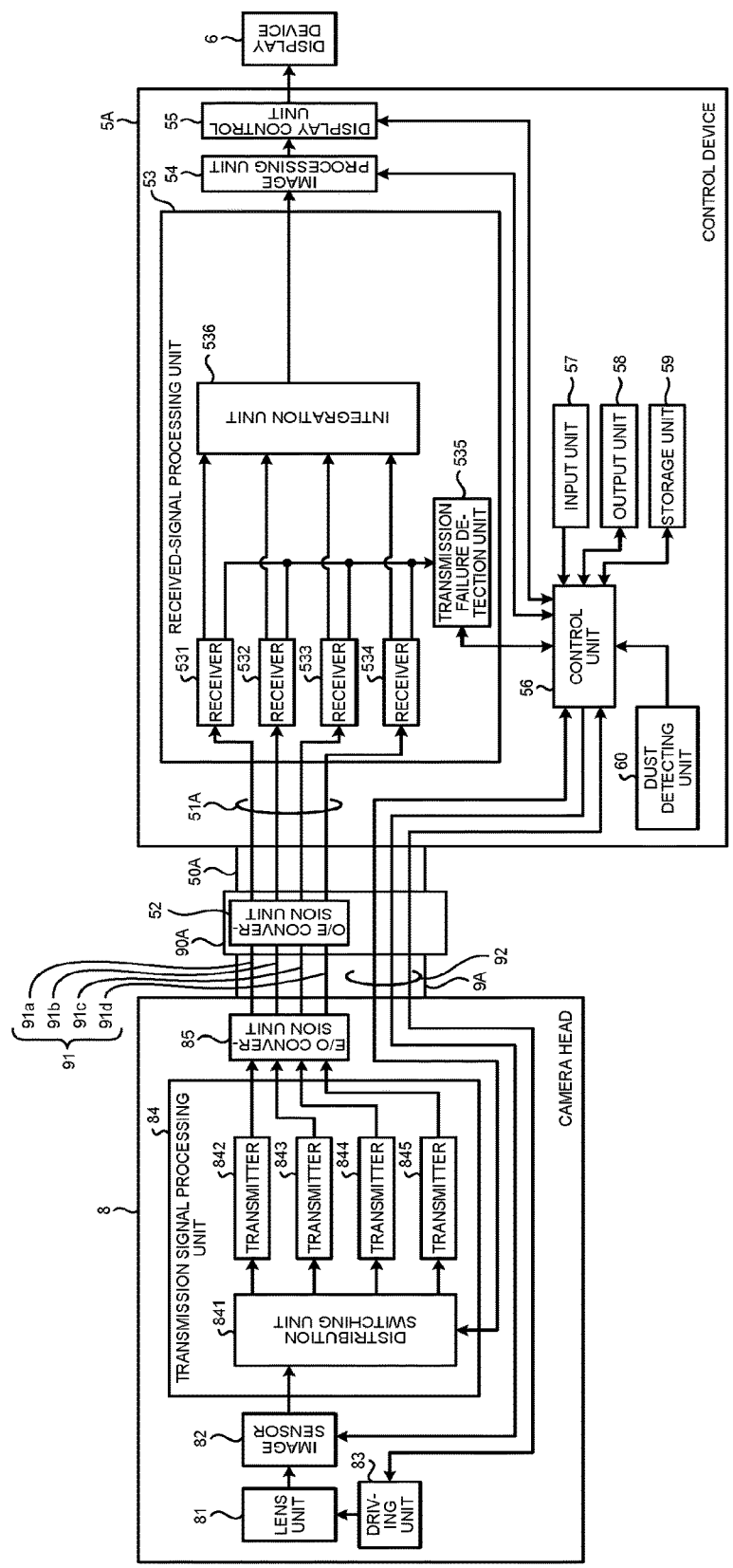
FIG. 8 is a block diagram of a configuration of a camera head, a transmission cable, and a control device of an endoscope according to a modification 1-1 of the first embodiment.

FIG. 8 is a block diagram of a configuration of a camera head, a transmission cable, and a control device of an endoscope according to a modification 1-1 of the first embodiment. In FIG. 8, compared to the configuration illustrated in FIG. 2, a connector 90A of a transmission cable 9A includes the O/E conversion unit 52, and a control device 5A does not include the O/E conversion unit 52. The respective optical signals transmitted through the optical cables 91a to 91d are converted into electrical signals by the O/E conversion unit 52 of the connector 90A, and the electrical signals are output to the received-signal processing unit 53 through four electrical wires 51A. Thus, according to the configuration illustrated in FIG. 8, by providing the O/E conversion unit 52 in the middle of the signal transmission paths, there is no need to provide the connector 90A and a connector 50A at the side of the control device 5A with the optical connection units 93a to 93d and 50a to 50d.

As the configuration illustrated in FIG. 8, when the connector 90A at the side of the transmission cable 9A includes the O/E conversion unit 52, signals can be transmitted from the transmission cable 9A to the control device 5A through the electrical wires. Thus, it is possible to prevent the transmission failure and image noise caused by, for example, the optical axis deviation in optical connection units and the soiled or fogged connection surfaces of the optical connection units.

Second Embodiment

A second embodiment will now be described. In the second embodiment, the optical cable group includes a spare optical cable. When a transmission failure occurs in one of the normally used optical cables, optical signals are transmitted using the spare optical cable, instead of using the optical cable in which the transmission failure has occurred.

Figure 9:
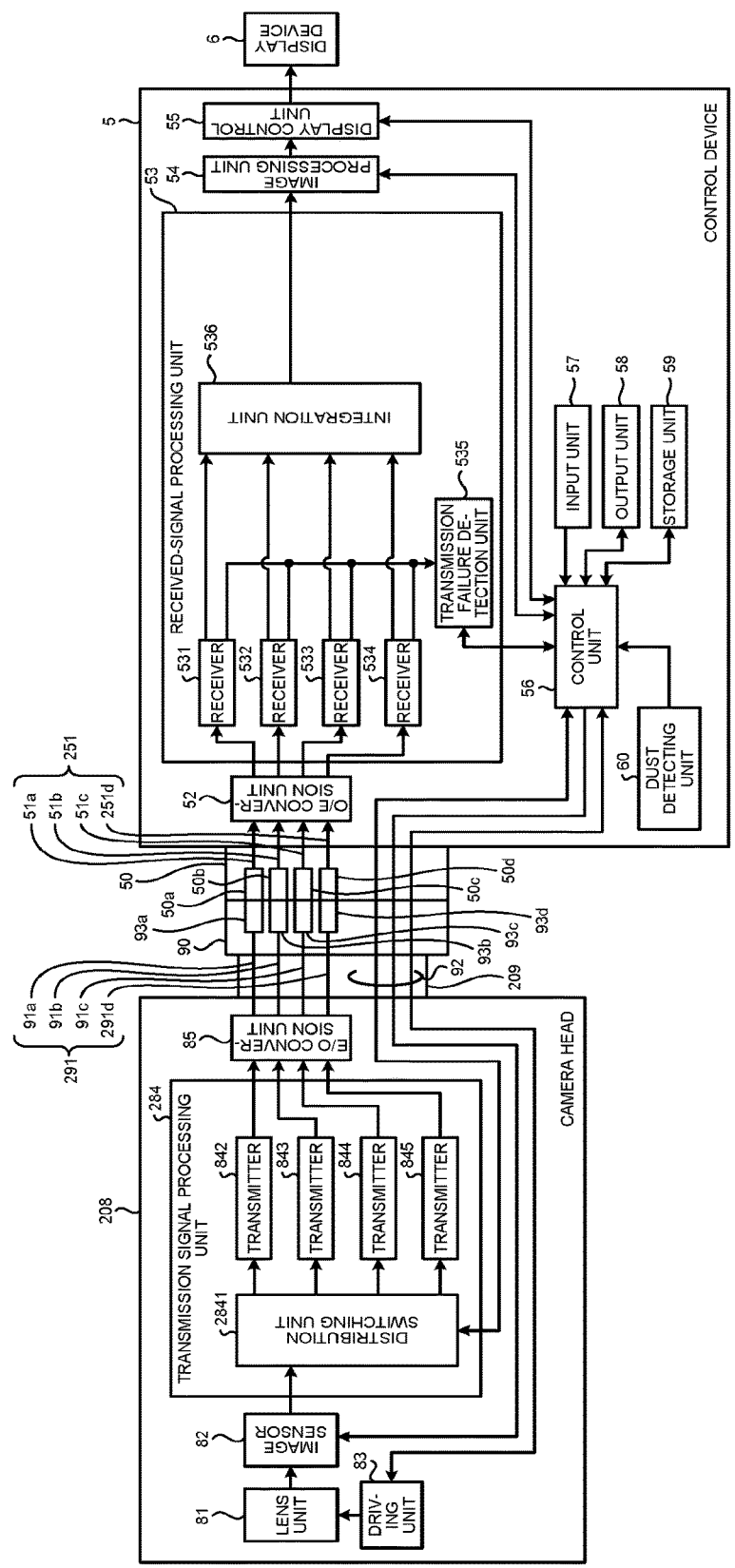
FIG. 9 is a block diagram of a configuration of a camera head, a transmission cable, and a control device of an endoscope according to a second embodiment of the present disclosure.

FIG. 9 is a block diagram of a configuration of a camera head, a transmission cable, and a control device of an endoscope according to a second embodiment. As illustrated in FIG. 9, a transmission cable 209 in the second embodiment includes a spare optical cable 291d in addition to the three normally used optical cables 91a to 91c as an optical cable group 291. The spare optical cable 291d can transmit at least one of the optical signals converted by the E/O conversion unit 85. In the transmission cable 209, the spare optical cable 291d is used to fill a gap between the other optical cables 91a to 91c, instead of a commonly used support material. An optical cable group 251 at the side of the control device 5 includes a spare optical cable 251d in addition to the three normally used optical cables 51a to 51c. Optical cables 51Y (Y=a, b, or c. Hereinafter, the same character is used in a corresponding manner) and 91Y, and optical connection units 50Y and 93Y each form a normally used signal transmission path. The spare optical cables 251d and 291d and the optical connection units 50d and 93d form a spare signal transmission path. In the second embodiment, the number of the normally used signal transmission paths may be two or four or more, and the number of the spare signal transmission path may be two or more.

A camera head 208 in the second embodiment includes a transmission signal processing unit 284. The transmission signal processing unit 284 includes a distribution switching unit 2841 and four transmitters 842 to 845. The transmission signal processing unit 284 functions as a medical signal processing device according to the present disclosure.

The distribution switching unit 2841 receives transmission failure information of a signal transmission path from the control device 5, and generates and outputs, to the four transmitters 842 to 845, the distribution image signals by switching the distribution method of the image signals based on the transmission failure information. For example, if the transmission state of all the signal transmission paths is normal, the distribution switching unit 2841 distributes the image signals output from the image sensor 82 to the three transmitters 842 to 844 corresponding to the three normally used signal transmission paths. The three signal transmission paths include optical cables 91a to 91c, respectively. If a transmission failure is detected in n pieces (n=1 or 2) of signal transmission paths among the three signal transmission paths, the distribution switching unit 2841 distributes the image signals to the transmitter 845 corresponding to the spare signal transmission path (including the spare optical cable 291d) and 3−n pieces of transmitters excluding the transmitters corresponding to the failed signal transmission paths. In the second embodiment, each of the image signals distributed by the distribution switching unit 2841 is also a parallel signal.

In the second embodiment, at most three serial electrical signals are input from the optical cable group 251 to the received-signal processing unit 53 of the control device 5.

In the second embodiment, for example, when the transmission failure detection unit 535 detects a transmission failure in the signal transmission path including the optical cable 91a among the normally used signal transmission paths, the control unit 56 transmits a distribution switching control signal to the distribution switching unit 2841 of the camera head 208. The distribution switching control signal causes the distribution switching unit 2841 to stop distributing the image signals to the transmitter 842 corresponding to the optical cable 91a, but to distribute the image signals to the transmitters 843 and 844 and the transmitter 845 corresponding to the spare signal transmission path.

In this manner, in the second embodiment, even if a transmission failure occurs in one of the three signal transmission paths during the procedure, the failed signal transmission path is switched to a transmission path that goes through the spare signal transmission path, in which no transmission failure has occurred. Because the optical signals are continuously transmitted as it is, it is possible to obtain the same advantages as those in the first embodiment.

If a transmission failure is detected in one of the three signal transmission paths, the transmission failure detection unit 535 may use a certain single signal transmission path, instead of using the remaining two signal transmission paths.

Modification 2-1 of Second Embodiment

Figure 10:
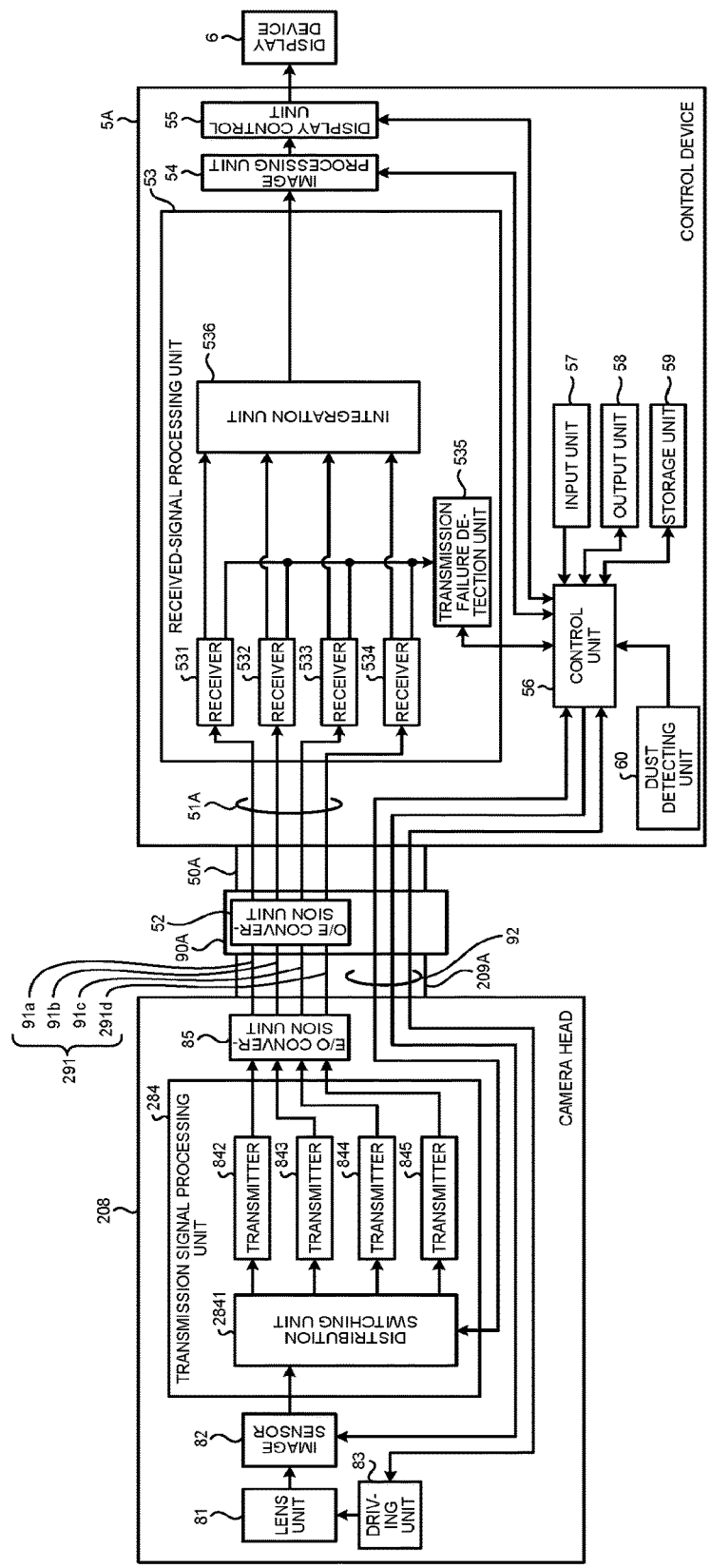
FIG. 10 is a block diagram of a configuration of a camera head, a transmission cable, and a control device of an endoscope according to a modification 2-1 of the second embodiment.

FIG. 10 is a block diagram of a configuration of a camera head, a transmission cable, and a control device of an endoscope according to a modification 2-1 of the second embodiment. As illustrated in FIG. 10, in the modification 2-1 of the second embodiment, the connector 90A of a transmission cable 209A includes the O/E conversion unit 52, and the control device 5A does not include the O/E conversion unit 52, as the configuration illustrated in the modification 1-1 of the first embodiment. In this case, similarly to the modification 1-1 of the first embodiment, signals can be transmitted from the transmission cable 209A to the control device 5A through the electrical wires. Thus, it is possible to prevent a transmission failure and image noise caused by, for example, the optical axis deviation in optical connection units and the soiled or fogged connection surfaces of the optical connection units.

Third Embodiment

A third embodiment of the present disclosure will now be described. In the following explanation, the same reference numerals are given to the same components as those in the first and the second embodiments described above, and the detailed description thereof will be omitted or simplified. In the medical observation systems 1 according to the first and the second embodiments described above, the present disclosure is applied to the endoscope 2 that uses the camera head 8. In a medical observation system according to the third embodiment, the present disclosure is applied to what is called a video scope that includes an image pickup unit at the tip end side of the inserting unit of the endoscope.

Figure 11:
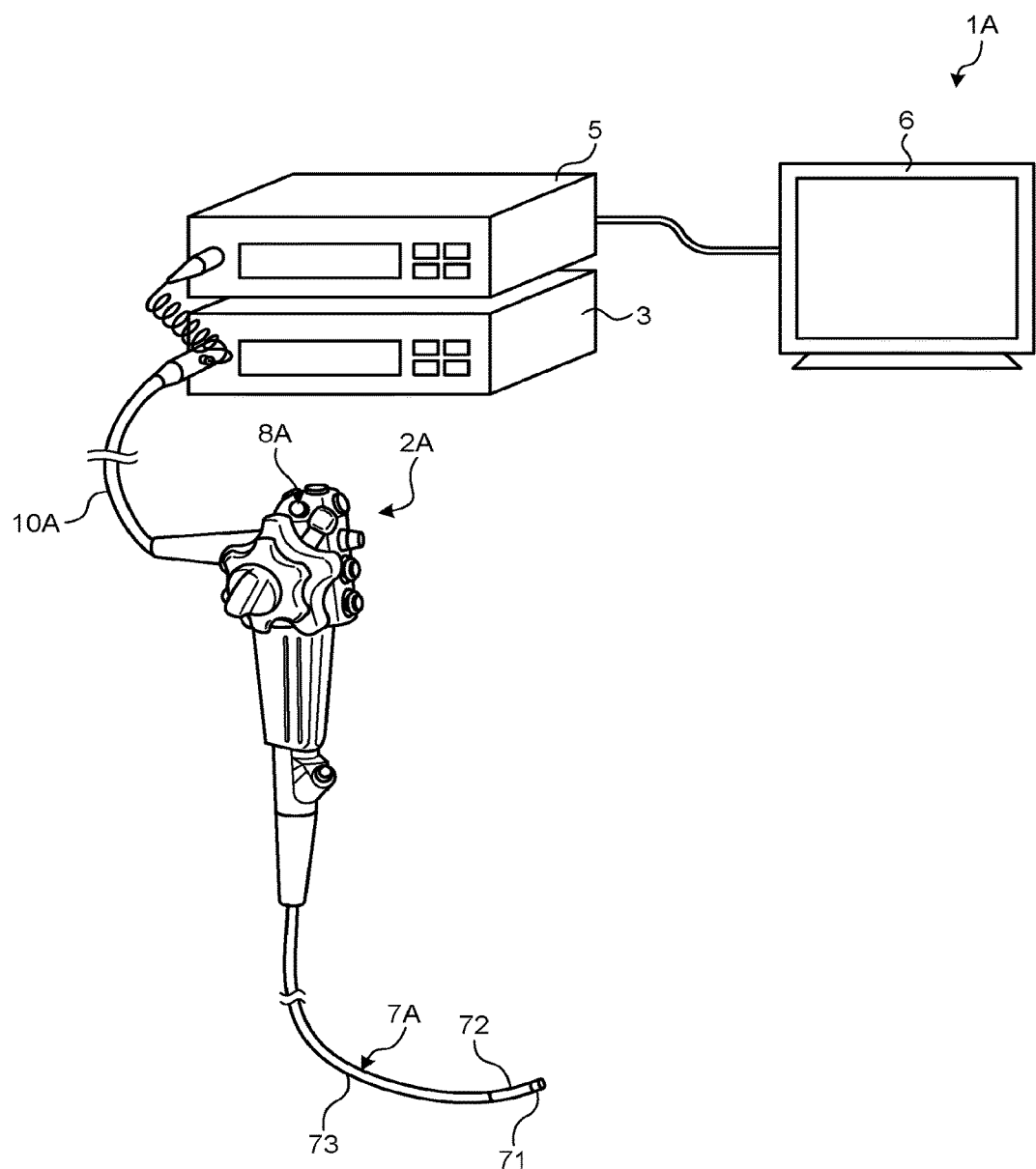
FIG. 11 is a schematic configuration diagram of a medical observation system according to a third embodiment of the present disclosure.

FIG. 11 is a schematic configuration diagram of a medical observation system according to the third embodiment of the present disclosure. As illustrated in FIG. 11, a medical observation system 1A according to the third embodiment includes an endoscope 2A, the light source device 3, the control device 5 (control device explained in the first or second embodiment described above), and the display device 6. The endoscope 2A generates an image signal by inserting an inserting unit 7A inside the body and picking up an in-vivo image of an observation portion and generates a plurality of image signals for transmission from the image signal. The light source device 3 generates illumination light output from the tip end of the endoscope 2A. The control device 5 receives the image signals for transmission generated by the endoscope 2A and processes the image signals for transmission. The display device 6 displays an image based on the video signals processed by the control device 5.

As illustrated in FIG. 11, the endoscope 2A includes the inserting unit 7A, an operating unit 8A, and a universal cord 10A. The inserting unit 7A has an elongated shape with flexibility. The operating unit 8A is connected to the base end side of the inserting unit 7A and receives an input of various types of operation signals. The universal cord 10A extends from the operating unit 8A in a direction different from that of the inserting unit 7A and includes various cables connected to the light source device 3 and the control device 5.

As illustrated in FIG. 11, the inserting unit 7A includes a tip end unit 71, a bending unit 72, and a flexible tube 73. The tip end unit 71 includes an image pickup unit (not illustrated) that picks up an image inside the body and generates an image signal. The bending unit 72 includes a plurality of bending pieces and is bendable. The flexible tube 73 is connected to the base end side of the bending unit 72 and has an elongated shape with flexibility.

Although FIG. 11 does not illustrate it in detail, the operating unit 8A includes the same components as those of the transmission signal processing unit 84 and the E/O conversion unit 85 explained in the first embodiment described above, and the image signal generated by the image pickup unit described above is processed by the transmission signal processing unit. The universal cord 10A also includes substantially the same components as those in the light guide 4 and the transmission cable 9 explained in the first embodiment described above. The image signals for transmission (optical signals) processed (generated) inside the operating unit 8A (transmission signal processing unit and electrical-to-optical conversion unit) are output to the control device 5 through the universal cord 10A.

Even if a soft endoscope (endoscope 2A) is used as in the third embodiment described above, it is possible to obtain the same advantages as those in the first embodiment described above.

Fourth Embodiment

A fourth embodiment of the present disclosure will now be described. In the following explanation, the same reference numerals are given to the same components as those in the first and the second embodiments described above, and the detailed description thereof will be omitted or simplified. In the medical observation system 1 according to the first and the second embodiments described above, the present disclosure is applied to the endoscope 2 that uses the camera head 8. In a medical observation system according to the fourth embodiment, the present disclosure is applied to a surgical operating microscope that picks up an image by enlarging a certain visual field area inside of a subject (inside the body) or on the surface of a subject (surface of the body).

Figure 12:
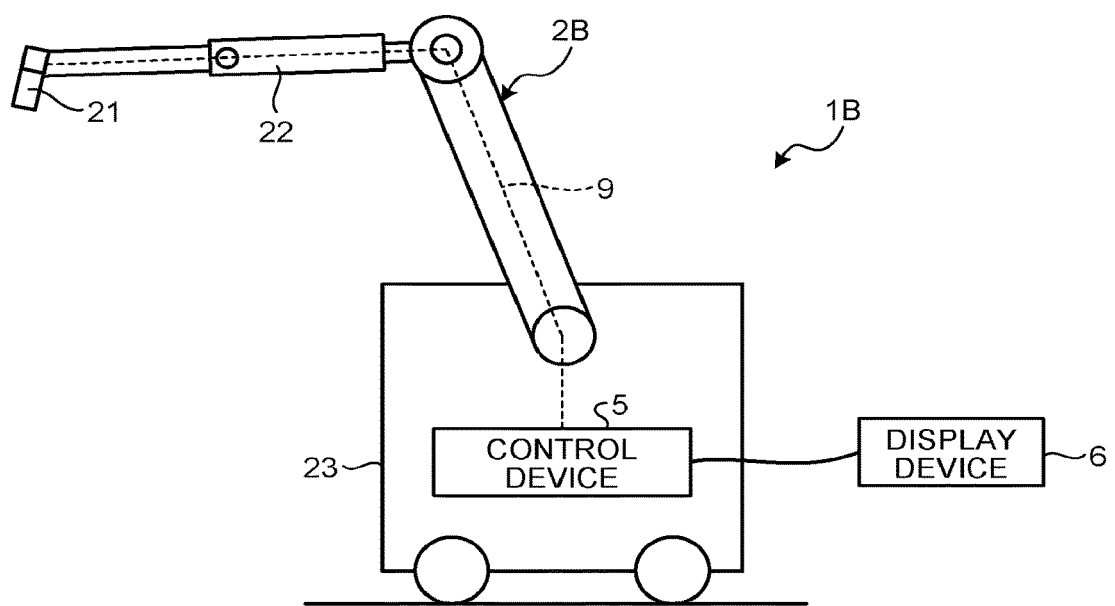
FIG. 12 is a schematic configuration diagram of a medical observation system according to a fourth embodiment of the present disclosure.

FIG. 12 is a schematic configuration diagram of a medical observation system according to the fourth embodiment of the present disclosure. As illustrated in FIG. 12, a medical observation system 1B according to the fourth embodiment includes a surgical operating microscope 2B, the control device 5 (control device explained in the first or second embodiment described above), and the display device 6. The surgical operating microscope 2B generates an image signal by picking up an image for observing a subject, and generates a plurality of image signals for transmission from the image signal. The control device 5 receives the image signals for transmission generated by the surgical operating microscope 2B and processes the image signals for transmission. The display device 6 that displays an image based on the video signals processed by the control device 5.

As illustrated in FIG. 12, the surgical operating microscope 2B includes a microscope unit 21, a supporting unit 22, and a base unit 23. The microscope unit 21 picks up an image by enlarging a micro-portion of a subject, generates an image signal, and generates a plurality of image signals for transmission from the image signal. The supporting unit 22 is connected to the base end of the microscope unit 21 and includes an arm that rotatably supports the microscope unit 21. The base unit 23 rotatably holds the base end of the supporting unit 22 and is movable on the floor surface. As illustrated in FIG. 12, the control device 5 is disposed on the base unit 23. The base unit 23 may be fixed to a ceiling, a wall, or other parts, instead of being provided on the floor surface in a movable manner, to support the supporting unit 22. The base unit 23 may include a light source unit that generates illumination light to be emitted from the surgical operating microscope 2B to the subject.

Although FIG. 12 does not illustrate it in detail, the microscope unit 21 includes the same components as those of the image pickup unit that generates an image signal by picking up an image inside the body or the surface of the body and the transmission signal processing unit 84 and the E/O conversion unit 85 explained in the first embodiment described above. The microscope unit 21 processes the image signal generated by the image pickup unit by the transmission signal processing unit. The image signals for transmission (optical signals) processed (generated) by the microscope unit 21 (transmission signal processing unit and electrical-to-optical conversion unit) are output to the control device 5 through the transmission cable 9 wired inside the supporting unit 22 along the supporting unit 22.

Even if the surgical operating microscope 2B is used as in the fourth embodiment described above, it is possible to obtain the same advantages as those in the first embodiment described above.

In the present disclosure, the distribution switching control performed by the distribution switching unit in the transmission signal processing unit of the camera head may be carried out in the camera head. In this case, the camera head performs the distribution switching control of the distribution switching unit, based on the transmission failure detection information received from the control device.

In the present disclosure, the signal transmission paths may transmit the electrical signals. In this case, the optical cable, the optical connection unit, the E/O conversion unit, and the O/E conversion unit described above become unnecessary, and the signal transmission paths are formed with the electrical wires and the connection unit that connects the electrical wires.

The medical observation system according to the present disclosure may include an ultrasonic endoscope that includes an ultrasonic probe instead of the endoscope described above.

A computer program for executing various processes in the camera head and the control device described above may be recorded on a computer-readable recording medium, such as a compact disc-read only memory (CD-ROM), a flexible disk, a compact disc-recordable (CD-R), or a digital versatile disc (DVD) as a file in an installable or an executable format. Furthermore, the computer program described above may be stored on a computer connected to a network such as the Internet, or may be provided through download over the network. The computer program may be provided or distributed over a network such as the Internet.

According to the present disclosure, it is possible to detect a transmission failure in an optical transmission path and to continuously transmit image signals to a control device, even if the transmission failure occurs in the optical transmission path.

It should be understood by those skilled in the art that various modifications, combinations, sub-combinations and alterations may occur depending on design requirements and other factors insofar as they are within the scope of the appended claims or the equivalents thereof.

What is claimed is:
1. A medical observation system, comprising:
a plurality of signal transmission paths configured to transmit a plurality of first signals;

a medical signal processing device that is configured to be connected to the plurality of signal transmission paths and to input parallel signals of image signals to the plurality of signal transmission paths as the plurality of first signals using a plurality of transmitters;

a medical control device configured to be connected to the plurality of signal transmission paths and including received-signal processing circuitry, wherein the received-signal processing circuitry receives the plurality of first signals from the plurality of signal transmission paths using a plurality of receivers and thereafter integrates the plurality of first signals transmitted through each signal transmission path, and wherein the medical signal processing device distributes the image signals to each signal transmission path when no transmission failure is detected and distributes the image signals to each signal transmission path, excluding a path where the transmission failure detected, when transmission failure is detected, and wherein the medical signal processing device further comprises electrical-to-optical conversion circuitry configured to convert a plurality of electrical signals based on the image signals into a plurality of optical signals and output the optical signals to the plurality of signal transmission paths.

2. The medical observation system according to claim 1, wherein the medical signal processing device is further configured to distribute the image signals so that a total transmission rate of the image signals for transmission is maintained regardless of a number of signal transmission paths.

3. The medical observation system according to claim 1, wherein
each of the plurality of signal transmission paths includes an optical cable configured to transmit an optical signal.

4. The medical observation system according to claim 3, wherein the medical control device further includes optical-to-electrical conversion circuitry configured to convert the optical signals into a plurality of electrical signals.

5. The medical observation system according to claim 3, wherein each of the plurality of signal transmission paths includes:
a plurality of the optical cables;
optical-to-electrical conversion circuitry configured to convert the optical signals into a plurality of electrical signals; and
a plurality of electrical wires configured to transmit the electrical signals.

6. The medical observation system according to claim 1, further comprising output circuitry configured to output, when the transmission failure is detected, information indicating that the transmission failure has occurred.

* * * * *